US005766193A

United States Patent [19]
Millner

[11] Patent Number: 5,766,193
[45] Date of Patent: Jun. 16, 1998

[54] TONGUE CLEANER

[76] Inventor: Don E. Millner, 212 Bruce Rd., Washington Crossing, Pa. 18977

[21] Appl. No.: 743,667

[22] Filed: Nov. 5, 1996

[51] Int. Cl.$^6$ .................................. A61B 17/24
[52] U.S. Cl. .................. 606/161; 606/162; 606/167
[58] Field of Search .................. 606/161, 162, 606/167

[56] References Cited

U.S. PATENT DOCUMENTS

| | | | |
|---|---|---|---|
| 1,891,864 | 12/1932 | Barrett | 606/161 |
| 2,218,072 | 10/1940 | Runnels | 606/161 |
| 2,583,750 | 1/1952 | Runnels | 606/161 |
| 3,890,964 | 6/1975 | Castanedo | 606/161 |
| 5,226,197 | 7/1993 | Nack et al. | 606/161 |
| 5,673,454 | 10/1997 | Quintanilla et al. | 606/161 |

*Primary Examiner*—Michael Buiz
*Assistant Examiner*—Daphna Shai
*Attorney, Agent, or Firm*—Donald S. Cohen

[57] ABSTRACT

A tongue scraper formed of a handle having a spoon shaped head at one end. The head has a relatively sharply rounded tip and increases in width from the tip to a mid-portion of the head. The head has substantially flat front and back surfaces. A scraper blade projects from the front surface and extends along the edge of the head from the tip to the mid-portion of the head. A plurality of scraper pins project from the front surface of the head and are arranged in a plurality of rows. The scraper pins have tapered top surfaces to provide them with a scraper edge. A plurality of holes extend through the head and are arranged in a plurality of rows. Each of the holes is of an area which can hold a liquid by capillary action.

8 Claims, 2 Drawing Sheets

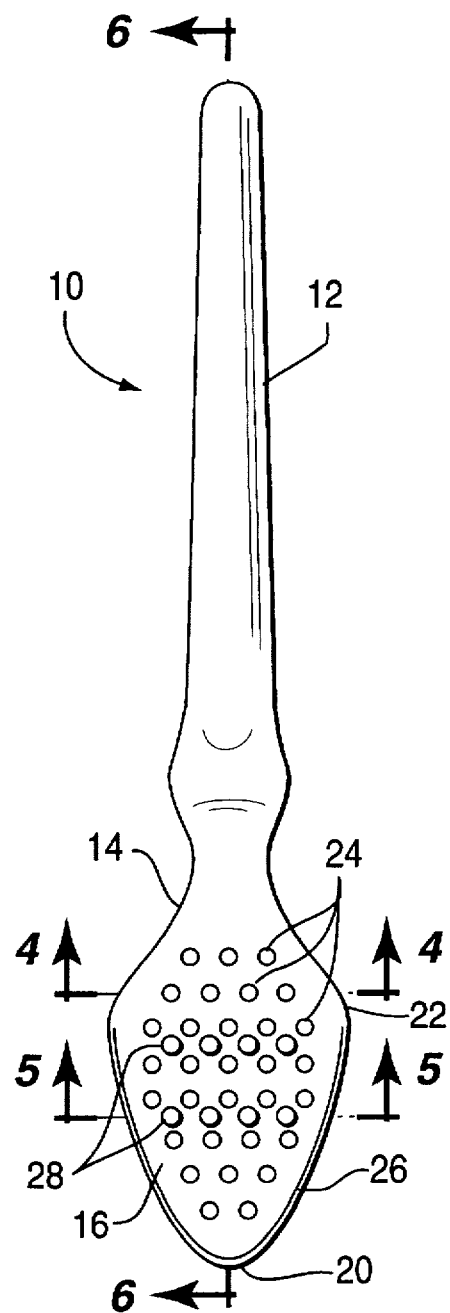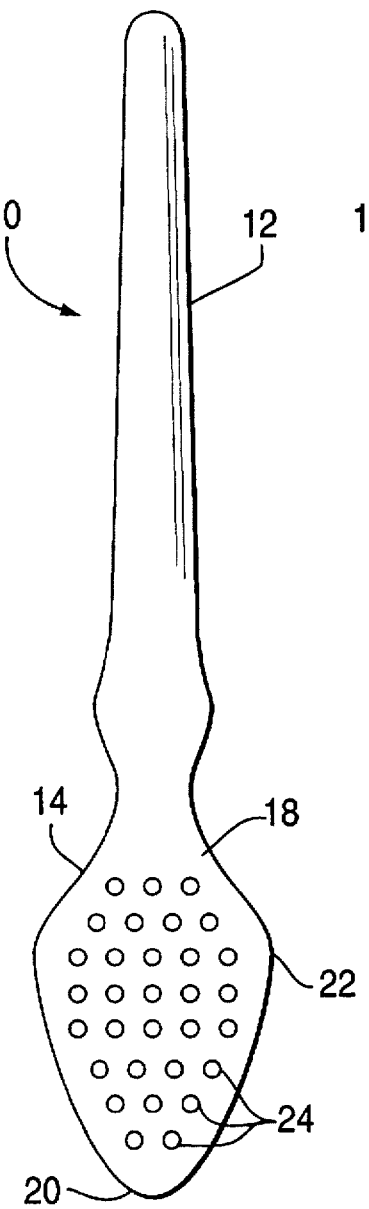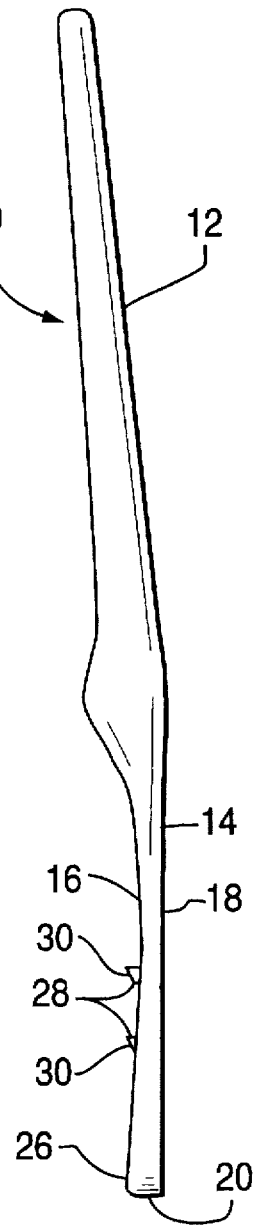
FIG. 1    FIG. 2    FIG. 3

TONGUE CLEANER

FIELD OF THE INVENTION

The present invention is directed to a tongue cleaner, and, more particularly, to a tongue cleaner which can hold a liquid medication or a mouth rinse.

BACKGROUND OF THE INVENTION

Most people believe that oral hygiene comprises cleaning the teeth and gums, and possibly rinsing the mouth with a cleaning solution. However, complete oral hygiene also includes the cleaning of the tongue. The physiology and anatomy of the tongue is such that it becomes a haven for germs. The physiology of the tongue is slightly furry in texture and has numerous projections, i.e., papillae, that become a breeding ground for bacteria to grow which allows greater opportunity for the collection of bacteria, food debris, dead cells and microorganisms, alive or dead. It is currently believed that such particles are the source of most bad breath in healthy individuals. Elimination of such particles from the surface of the tongue, therefore, is important for the reduction of oral odors and overall mouth cleaning and hygiene.

Although there are presently available devices for cleaning the tongue, they are in general a rigid handle having some type of scraper on the end thereof. For example, U.S. Pat. No. 5,217,475 to D. U. Kuper, issued Jun. 8, 1993, entitled TONGUE SCRAPERS, discloses a tongue scraper which has on the end of a handle a blade having a serrated edge. the blade is bent into a U and the ends are secured to the ends of a forked portion of the handle. The blade is pulled across the tongue, from back to front, to remove material from the tongue. U.S. Pat. No. 5,226,197 to R. Nack et al., issued Jul. 13, 1993, entitled TONGUE HYGIENE DEVICE, discloses a tongue cleaner which includes a rigid handle having a flat wider portion at one end. A plurality of spaced bristle extend from the flat portion and a semi-rigid band is secured around the end of the flat portion. This device is also moved across the tongue, generally from back to front to clean the tongue. U.S. Design Pat. No. 291,001 to J. Gaskins, issued Jul. 21, 1987, entitled TONGUE SCRAPER, shows a device having a rigid handle and a flat portion at one end. A plurality of curved projections extend from the flat portion. This device, apparently is moved across the tongue from back to front to remove material from the tongue.

Although the scraper type of tongue cleaners described in the above patents do remove undesirable material from the tongue, they may not be efficient and may contribute to a gag response. Therefore, it is desirable to have a tongue cleaner which is more efficient in the ability to remove undesirable particles from the tongue, provide a reduced gag response and provide a means to substantially and efficiently deliver a liquid mouth rinse that would reduce bad breath at the site that it is needed the most.

SUMMARY OF THE INVENTION

A tongue cleaner includes a handle having a relatively flat head at one end thereof. The head has front and back surfaces and a tip. A scraper blade projects from the front surface of the head and extends along the edge of the head and around the tip. A plurality of pins project from the front surface of the head, each of the pins has a scraper edge.

Another version of the tongue cleaner includes a handle having a relatively flat head at one end thereof. The head has front and back surfaces and a tip. A scraper blade projects from the front surface of the head and extends along the edge of the head and around the tip. A plurality of holes extend through the head and each of the holes is of an area which can hold a liquid by capillary action.

Still another version of the tongue cleaner includes a handle having a relatively flat head at one end thereof. The head has front and back surfaces and a relatively sharply rounded tip. A scraper blade projects from the front surface of the head and extends along the edge of the head and around the tip.

BRIEF DESCRIPTION OF THE DRAWINGS

FIG. 1 is a front plan view of the tongue scraper of the present invention;

FIG. 2 is a back plan view of the tongue scraper of the present invention;

FIG. 3 is a side view of the tongue scraper of the present invention;

DETAILED DESCRIPTION

Figure 4:
Figure 5:
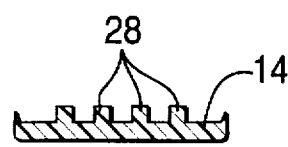
FIG. 5 is a sectional view taken along line 5—5 of FIG. 1.

Referring initially to FIGS. 1, 2 and 3, the tongue cleaner of the present invention is generally designated as 10. Tongue cleaner 10 comprises a handle 12 having a relatively flat head 14 at one end thereof. The tongue cleaner 10 is made of a relatively rigid solid material, such as a plastic. The head 14 has a front surface 16 and a back surface 18, and is relatively spoon shape. The head 14 has a relatively sharply rounded tip 20 and increases in width to its mid-portion 22 and then tapers down in width to the handle 12. The head 14 has a plurality of holes 24 therethrough which are arranged in a plurality of rows across the head 14. The holes 24 are of a size such that they can hold a liquid medication or mouth cleaner by capillary action. For example, the holes 24 can be of an area of between about 0.002 and 0.008 square inches.

Figure 6:
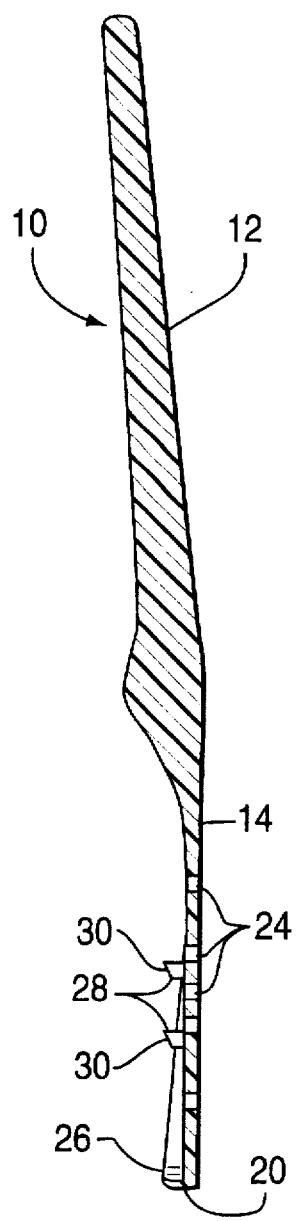
FIG. 6 is a sectional view taken along line 6—6 of FIG. 1.

A scraper blade 26 projects outwardly from the front surface 16 of the head 14 and extends along the edge of the head 14 from the tip 20. The height of the blade 26, i.e., its dimension from the front surface 16 of the head 14, varies along the edge of the head 14. As shown in FIG. 6, the height of the blade 26 is greatest at the tip 20 of the head 14 and tapers down to the front surface 16 at substantially the mid-portion 22 of the head 14.

A plurality of scraper pins 28 project from the front surface 16 of the head 14. The pins 28 are arranged in rows across the head 14 between the rows of holes 24. Although only two rows of pins 28 are shown, there can be more rows of the pins if desired. As shown in FIG. 6, the top surfaces 30 of the pins 28 are tapered to provide a sharp edge. Also, the pins 28 which are closer to the tip 20 of the head 14 are longer than the pins 28 which are closer to the mid-portion of the head 14. If additional rows of the pins 28 were provided, their length would be different depending on their position on the head 14.

In the use of the tongue cleaner 10, the head 14 is dipped into a container of a liquid medication or mouth cleaner so that the holes 24 become filled with the liquid by capillary action. The head 14 is then placed in the mouth of the user with the blade 20 and scraper pins 28 contacting the tongue of the user. The head 14 is then moved across the tongue to scrape the tongue with the blade 20 and scraper pins 28 and thereby clean the tongue. The curved shape of the blade 20 and its variation in height provides a better fit of the blade along the tongue so as to achieve a good scraping. The pins 28 provide a disruption of the debris on the tongue and the blade serves to scrape and provide a collection of the broken debris. The rounded tip of the blade 20 allows the blade to reach farther to the back of the tongue and yet minimize provoking any gag reflex. At the same time, the medicine or mouth cleaner is brought into contact with the scraped tongue so as to deodorize and cleanse the tongue. Thus, the tongue cleaner 10 of the present invention provides both a scraping of the tongue to clean the tongue and mouth cleaner for deodorizing the tongue and mouth.

Figure 7:
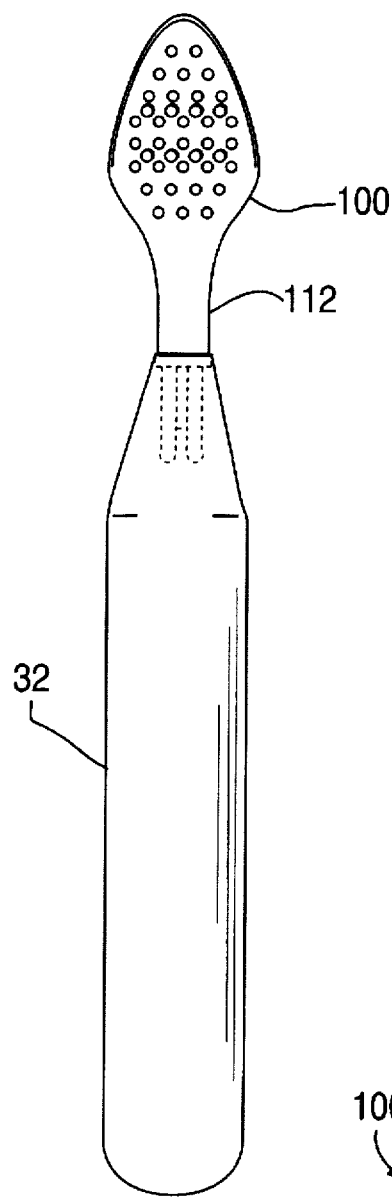
FIG. 7 is a plan view of a form of the tongue scraper of the present invention which is mounted on a vibrating handle.
Figure 8:
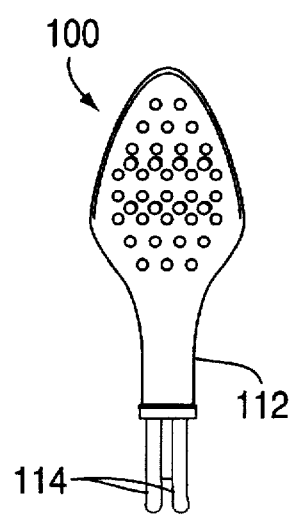
FIG. 8 is a plan view of the tongue cleaner which can be mounted on a vibrating handle.

Referring to FIG. 7, there is shown a form of the tongue cleaner of the present invention, generally designated as 100, which is adapted to be mounted on the end of housing 32 which contains means for moving the head, such as a sonically resonating motor, not shown. Such a structure of a housing is shown and described in U.S. Pat. No. 5,123,841 (Millner), issued Jun. 23, 1992, which is incorporated herein by reference. The tongue cleaner is removably mounted on the end of the housing 32 so that it can be moved by the means within the housing. The tongue cleaner 100 is identical to the tongue cleaner 10, shown in FIGS. 1-3, except that instead of having an elongated handle 12, it has a shorter handle 112 with a pair of prongs 114 extending therefrom as shown in FIG. 8. The prongs 114 fit into slots in the end of the housing 32 to connect the tongue cleaner 100 to the moving means in the housing 32. The tongue cleaner 100 is used in the same manner as described above with regard to the tongue cleaner 10. However, as the tongue cleaner is moved across the tongue, it is placed in motion by the means in the housing 32 so as to provide additional scraping action.

Thus, there is provided by the present invention a tongue cleaner having a tongue scraper blade projecting from and extending around the edge of a spoon shaped head with the height of the blade tapering down from its highest at the tip of the head to substantially the mid-portion of the head. A plurality of scraper pins project from the head and have tapered ends to provide the pins with a scraping surface. The head has a plurality of holes therethrough which are of an area to hold a liquid, such as a medicine or mouth cleaner, by capillary action. This provides for good cleaning of the tongue by scraping and provides a medicine or mouth cleaner at the same time to clean and deodorize the tongue. Although the scraper pins 28 and holes 24 are shown as to be round in cross-section, they can be of any desired shaped, such as square, triangular, etc. Also, the number of scraper pins 28 and holes 24 can vary from that shown.

What is claimed is:

1. A tongue cleaner comprising:
    a handle;
    a relatively flat head at one end of the handle, said head having front and back surfaces and a tip;
    a scraper blade projection from the front surface of the head and extending along the edge of the head and around the tip; and
    a plurality of holes through said head, each of the holes being of an area which can hold a liquid by capillary action.

2. A tongue cleaner in accordance with claim 1 in which the holes are arranged in rows across the head.

3. A tongue cleaner in accordance with claim 2 in which the head has a rounded tip and increases in width from the tip to a mid-portion of the head, and the scraper blade extends along the edge of the head from the tip to substantially the mid-portion of the head.

4. A tongue cleaner in accordance with claim 3 in which the height of the scraper blade is greatest at the tip and decreases in each direction along the edge of the head to substantially the mid-portion of the head.

5. A tongue scraper in accordance with claim 4 further comprising a plurality of scraper pins projecting from the front surface of the head, each of the scraper pins having a scraper edge.

6. A tongue scraper in accordance with claim 5 in which the top surface of each of the pins is tapered to provide the scraper edge.

7. A tongue cleaner in accordance with claim 6 in which the scraper pins are arranged in rows across the front surface of the head and the height of the pins varies from the rows adjacent the tip of the head to the rows adjacent the mid-portion of the head.

8. A tongue cleaner in accordance with claim 7 in which the height of the pins decreases from the rows adjacent the tip of the head to the rows adjacent the mid-portion of the head.

* * * * *